United States Patent
Harriman et al.

(10) Patent No.: US 11,033,009 B2
(45) Date of Patent: Jun. 15, 2021

(54) TRANSGENIC CHICKEN FOR PRODUCTION OF ANTIBODIES HAVING A COMMON LIGHT CHAIN

(71) Applicant: Crystal Bioscience Inc., San Diego, CA (US)

(72) Inventors: William Don Harriman, Alameda, CA (US); Robert Etches, Oakland, CA (US); Philip A. Leighton, San Francisco, CA (US)

(73) Assignee: CRYSTAL BIOSCIENCE INC., San Diego, CA (US)

( * ) Notice: Subject to any disclaimer, the term of this patent is extended or adjusted under 35 U.S.C. 154(b) by 174 days.

(21) Appl. No.: 15/753,938

(22) PCT Filed: Aug. 24, 2016

(86) PCT No.: PCT/US2016/048485
§ 371 (c)(1),
(2) Date: Feb. 20, 2018

(87) PCT Pub. No.: WO2017/035274
PCT Pub. Date: Mar. 2, 2017

(65) Prior Publication Data
US 2018/0249687 A1   Sep. 6, 2018

Related U.S. Application Data

(60) Provisional application No. 62/210,926, filed on Aug. 27, 2015.

(51) Int. Cl.
*A01K 67/027* (2006.01)
*C12N 15/85* (2006.01)
*C07K 16/00* (2006.01)
*C07K 16/46* (2006.01)

(52) U.S. Cl.
CPC .......... *A01K 67/0278* (2013.01); *C07K 16/00* (2013.01); *C07K 16/46* (2013.01); *C12N 15/8509* (2013.01); *A01K 2217/072* (2013.01); *A01K 2217/206* (2013.01); *A01K 2227/30* (2013.01); *A01K 2267/01* (2013.01); *C07K 2317/21* (2013.01); *C07K 2317/23* (2013.01); *C12N 2800/30* (2013.01); *C12N 2830/40* (2013.01)

(58) Field of Classification Search
CPC ............ A01K 67/0278; A01K 2227/30; A01K 2267/01; C07K 16/46
USPC ....................................... 800/18, 21
See application file for complete search history.

(56) References Cited

U.S. PATENT DOCUMENTS

| 8,592,644 | B2 | 11/2013 | Harriman et al. | |
| 9,380,769 | B2* | 7/2016 | Leighton | A01K 67/0276 |
| 9,394,372 | B2 | 7/2016 | Harriman | |
| 9,809,642 | B2* | 11/2017 | Leighton | A01K 67/0276 |
| 2011/0236378 | A1 | 9/2011 | Green et al. | |
| 2014/0068796 | A1 | 3/2014 | Harriman et al. | |

FOREIGN PATENT DOCUMENTS

WO   WO 99/45962   9/1999

OTHER PUBLICATIONS

Oishi (Scientific Reports, Apr. 2016, vol. 6 23980, p. 1-10).*
Park, "Deposition of bioactive human epidermal growth factor in the egg white of transgenic hens using an oviduct-specific minisynthetic promoter." FASEB J. 29, 2386-2396 (2015).*
Schusser, Immunoglobulin knockout chickens via efficient homologous recombination in primordial germ cells. Proc Natl Acad Sci USA 110, 20170-20175 (2013).*
Park, "Targeted gene knockout in chickens mediated by TALENs." Proc Natl Acad Sci USA 111, 12716-12721 (2014).*
Park (PNAS, Jun. 12, 2012, vol. 109, No. 24, 9337-9341).*
Rattcliff (Developmental and Comparative Immunol., 2006, vol. 30, p. 101-118).*
Ching (mAbs, 2018, vol. 10, No. 1, p. 71-80).*
Fischer et al, "Exploiting light chains for the scalable generation and platform purification of native human bispecific IgG", Nature Communications, 2015, 6:6113.
"Chicken germline Ig light chain gene VJC region, complete cds", GenBank: M24403.1, 1993, Nucleotide—NCBI.
Van de Lavoir, et al., "Germline transmission of genetically modified primordial germ cells", Nature, 2006, 441:766-769.
Leighton, et al., "Genetic modification of primordial germ cells by gene trapping, gene targeting, and phiC31 Integrase", Mol Reprod & Dev, 2008, 75:1163-75.
Schusser et al., "Immunoglobulin knockout chickens via efficient homologous recombination in primordial germ cells", PNAS, 2013, 110(50): 20170-20175.

* cited by examiner

Primary Examiner — Michael C Wilson
(74) Attorney, Agent, or Firm — James S. Keddie; Bozicevic, Field & Francis LLP (57) ABSTRACT

This disclosure provides, among other things, a transgenic animal and a method of using the same to make antibodies that have a common light chain. In certain embodiments, the transgenic animal may comprising a genome comprising a common light chain transgene, wherein the common light chain transgene comprises a non-immunoglobulin light-chain promoter and a common light-chain coding sequence. In certain embodiments, the common light chain is constitutively expressed.

7 Claims, 7 Drawing Sheets

TRANSGENIC CHICKEN FOR PRODUCTION OF ANTIBODIES HAVING A COMMON LIGHT CHAIN

CROSS-REFERENCING

This application is a § 371 national phase of International Application No. PCT/US2016/048485, filed on Aug. 24, 2016, which claims the benefit of U.S. provisional application Ser. No. 62/210,926, filed on Aug. 27, 2015, which applications are incorporated herein by reference.

BACKGROUND

Classical antibodies are composed of two identical heavy-chains, each of which forms a heterodimer with a common light-chain. In contrast, bispecific antibodies can have two different heavy-chains and two different light-chains and each pair will bind a different antigen. Random association of two different light-chains and two different heavy-chains produces a mixture of many combinations of the component chains. Typically, only a small fraction of the combinations will produce a functional antibody, each of which recognizes a target antigen. The ability to bind two antigens has been used to co-localize components of the clotting cascade by mimicking Factor VIII (Sampei et al., PLoS One. 2013, 8(2):e57479), targeting T cells to tumor cells (Frankel and Baeuerle, Curr. Opin. Chem. Biol. 2013, 17(3):385-392) and chaperoning therapeutics across the blood-brain barrier (Bien-Ly et al., J. Exp. Med. 2014, 211(2):233-244).

The many approaches to manufacture a consistent product by restricting the number of potential associations in bispecific antibodies are described in Spiess et al., Mol. Immunol. 2015, 67(2 Pt A):95-106). In one approach, a common heavy-chain that dimerizes with different light-chains has been created (Fischer et a., Nat. Communications. 2015, 6:6113). In another approach, a common light-chain that dimerizes with different heavy-chains has been created (U.S. Patent Application Nos. 2014/0314755 and 2011/0195454)

Antibodies recognize epitopes on antigens and within each antigen, there are a finite number of epitopes. In practice, the number of epitopes that can be revealed is restricted by the evolutionary distance between the source of the antigen and the animal in which the antigen is introduced. Typically, the source of the antigen is human when the objective is the generation of a therapeutic, and typically, the animal in which the antigen is introduced is murine. The evolutionary distance can be increased by using animals that are further away from each other evolutionarily than the human-murine relationship (murine and human lineages separated approximately 95 million years ago). For example, evolutionary distance can be increased by immunizing chickens, which last shared a common ancestor with humans approximately 300 million years ago. It has been shown that approximately 30% of the antibodies that are derived from immunized chickens are directed at epitopes that are not revealed by members of panels of murine hybridomas.

While chicken antibodies are useful because they recognize unique epitopes, they are foreign proteins when considered for use as therapeutics. Patients will raise anti-chicken variable (V) region antibodies even if the chicken antibody has been grafted onto human constant (C) regions, resulting in a loss of therapeutic efficacy. This issue can be solved by replacing the endogenous chicken immunoglobulin heavy- and light-chain V genes with human equivalents, such that resulting transgenic chickens produce human antibodies.

Certain aspects of this disclosure relate to a transgenic animal that produces a common light-chain with a pre-arranged variable region and methods of using the same for the production of bispecific antibodies. In some aspects, the transgenic animal is a transgenic bird, e.g., chicken.

SUMMARY

This disclosure provides, among other things, a transgenic animal comprising a genome comprising a common light chain transgene, wherein the common light chain transgene comprises a non-immunoglobulin light-chain promoter and a common light-chain coding sequence. In certain embodiments, the common light chain is constitutively expressed.

In certain embodiments the transgenic animal comprises a genome comprising: a) a recombinase transgene, wherein the recombinase transgene comprises a recombinase coding sequence operably linked to an endogenous immunoglobulin light-chain promoter; and b) a recombinase inducible common light-chain transgene comprising: i. a non-immunglobulin light-chain promoter; ii. a common light-chain coding sequence and iii. an intervening sequence that prevents the common light-chain from being expressed, unless the intervening sequence is excised by recombinase.

To produce a bi-specific antibody, it is advantageous if the light chain is common to both branches of the antibody molecule, with the binding specificity determined solely by the heavy chain. The light chain provides the proper structure for assembly of the full antibody molecule but is a passive partner for antigen binding. Expression of the bi-specific is thus simplified because it only requires the two heavy chains and the one, common light chain.

Normally, light chain genes undergo mutational processes during B cell development to produce a diverse repertoire of sequences, and further diversification and selection during an immune response to refine and improve antigen binding. The common light chain approach aims to avoid any and all mutation so that the light chain remains unchanged in B cells. One of the drivers of diversity is the process of gene rearrangement in which one of the various V regions combines with one of the various J regions in an imprecise process which produces variation at the V-J junction, forming the important CDR3 loop. The common light chain approach bypasses this step and expresses a pre-rearranged variable region with the same sequence in all B cells. The second major source of diversity in chickens is from gene conversion by upstream pseudogenes which donate sequences to the functional V. Without any upstream pseudogenes, no gene conversion can occur.

Figure 1:
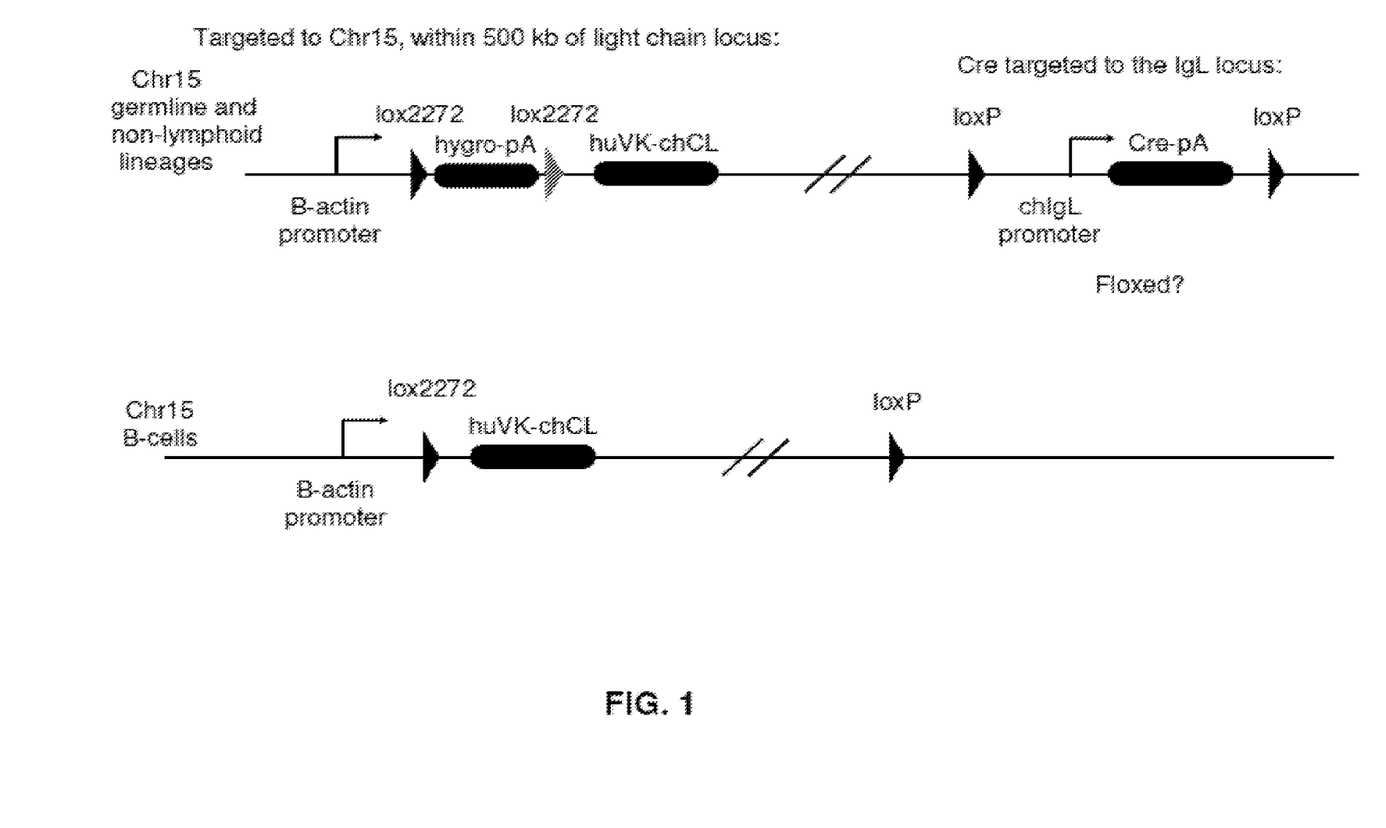
FIG. 1 depicts a schematic showing a strategy to achieve B cell specific expression of common light-chain. In this strategy, B-cell specific Cre expression leads to loop out of Cre and STOP cassette, leading to expression of huVK. If leaky Cre expression is a concern, leading to loss of Cre before hygro-pA is removed, could make it without floxing Cre itself. Continued Cre expression in B cells would make sure that loop out of hygro-pA is complete.

Since the mechanisms of antibody diversification in B cells are mainly confined to genes in the immunoglobulin loci, one approach to making a transgenic animal, e.g., a chicken with a common light chain that does not undergo mutation, is to insert the light chain in another locus in the genome, under transcriptional control of non-immunoglobin control elements (FIG. 1). B cell-specific expression is achieved using a conditional transgene that is activated upon recombinase mediated recombination only in B cells. To achieve recombinase-mediated recombination only in B cells, recombinase expression is made B cell-specific by inserting the recombinase gene in the light chain locus. Upon induction of recombinase expression by the light chain regulatory elements in early B cell development, the recombinase activity loops out a stop sequence that blocks expression of the common light chain. The recombinase gene could potentially suffer from mutations that compromise its activity since it is located in the light chain locus, but active recombinase is produced early enough, prior to significant inactivating mutations, to perform the loop out. Once the loop out has occurred, the recombinase is no longer needed. In fact, continued high-level recombinase expression is not preferred because it could have potential deleterious effects on B cell function. Thus a self-inactivating recombinase transgene is preferred, e.g., one that contains recombination sites (e.g., loxP sites) that flank the recombinase (Cre) gene. The recombinase gene is stable and present in the germline, which is critical for germline transmission and establishing fully transgenic chickens carrying the transgene, because the light chain regulatory elements do not drive expression of the recombinase in the germline. In the B-cell lineage, recombinase activity is induced, causing activation of the common light chain and simultaneously deletion of the recombinase gene.

A potentially simpler approach might be to insert the pre-rearranged V region in the light chain locus, and remove all pseudogenes upstream, eliminating the possibility of gene conversion. However, this approach is likely to lead to significant mutation of the light chain and defeat the purpose of the common light chain strategy. Although gene conversion provides the bulk of the naïve, pre-immune diversity in wild type cells, in the absence of pseudogenes there is a shift to somatic hypermutation. It has also been shown in mice that pre-rearranged variable regions, when inserted in the immunoglobulin loci, undergo somatic mutation.

DEFINITIONS

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Determining the presence of" includes determining the amount of something present, as well as determining whether it is present or absent.

The term "gene" refers to a nucleic acid sequence comprised of a promoter region, a coding sequence, and a 3' UTR.

The terms "protein" and "polypeptide" are used interchangeably herein.

The term "nucleic acid" encompasses DNA, RNA, single stranded or double stranded and chemical modifications thereof. The terms "nucleic acid" and "polynucleotide" are used interchangeably herein.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). Similarly, when an intron is operably-linked to a coding sequence, the intron is spliced out of the mRNA to provide for expression of the coding sequence. "Unlinked" means that the associated genetic elements are not closely associated with one another and the function of one does not affect the other.

The term "homozygous" indicates that identical alleles reside at the same loci on homologous chromosomes. In contrast, "heterozygous" indicates that different alleles reside at the same loci on homologous chromosomes. A transgenic animal may be homozygous for a transgene, or hemizygous for a transgene if there is no counterpart at the same locus on the homologous chromosome.

The term "endogenous", with reference to a gene, indicates that the gene is native to a cell, i.e., the gene is present at a particular locus in the genome of a non-modified cell. An endogenous gene may be a wild type gene present at that locus in a wild type cell (as found in nature). An endogenous gene may be a modified endogenous gene if it is present at the same locus in the genome as a wild type gene. An example of such a modified endogenous gene is a gene into which a foreign nucleic acid is inserted. An endogenous gene may be present in the nuclear genome, mitochondrial genome etc.

The term "construct" refers to a recombinant nucleic acid, generally recombinant DNA, that has been generated for the purpose of the expression of a specific nucleotide sequence(s), or is to be used in the construction of other recombinant nucleotide sequences. A construct might be present in a vector or in a genome.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide. If a cell receives a recombinant nucleic acid, the nucleic acid is "exogenous" to the cell.

The term "selectable marker" refers to a protein capable of expression in a host that allows for ease of selection of those hosts containing an introduced nucleic acid or vector. Examples of selectable markers include, but are not limited to, proteins that confer resistance to antimicrobial agents (e.g., hygromycin, bleomycin, or chloramphenicol), proteins that confer a metabolic advantage, such as a nutritional advantage on the host cell, as well as proteins that confer a functional or phenotypic advantage (e.g., cell division) on a cell.

The term "expression", as used herein, refers to the process by which a polypeptide is produced based on the nucleic acid sequence of a gene. The process includes both transcription and translation.

The term "introducing" in the context of inserting a nucleic acid sequence into a cell, includes "transfection" and "transformation" and all other methods of introducing a nucleic acid into a cell, where the nucleic acid sequence may be incorporated into the genome of the cell (e.g., chromosome, plasmid, plastid, or mitochondrial DNA) or converted into an autonomous replicon, or transiently expressed.

The term "coding sequence" refers to a nucleic acid sequence that once transcribed and translated produces a protein, for example, in vivo, when placed under the control of appropriate regulatory elements. A coding sequence as used herein may have a continuous ORF or might have an ORF interrupted by the presence of introns or non-coding sequences. In this embodiment, the non-coding sequences are spliced out from the pre-mRNA to produce a mature mRNA.

The term "replacing", in the context of replacing one genetic locus with another, refers to a single step protocol or multiple step protocol.

The term "introduced" in the context of inserting a nucleic acid sequence into a cell, means "transfection", or 'transformation", or "transduction" and includes reference to the incorporation of a nucleic acid sequence into a eukaryotic or prokaryotic cell wherein the nucleic acid sequence may be present in the cell transiently or may be incorporated into the genome of the cell (e.g., chromosome, plasmid, plastid, or mitochondrial DNA), converted into an autonomous replicon.

The term "introduced" in the context of inserting a nucleic acid sequence into a cell, means "transfection", or 'transformation", or "transduction" and includes reference to the incorporation of a nucleic acid sequence into a eukaryotic or prokaryotic cell wherein the nucleic acid sequence may be present in the cell transiently or may be incorporated into the genome of the cell (e.g., chromosome, plasmid, plastid, or mitochondrial DNA), converted into an autonomous replicon.

The term "plurality" refers to at least 2, at least 5, at least 10, at least 20, at least 50, at least 100, at least 200, at least 500, at least 1000, at least 2000, at least 5000, or at least 10,000 or at least 50,000 or more. In certain cases, a plurality includes at least 10 to 50. In other embodiments, a plurality may be at least 50 to 1,000.

As used herein, the term "isolated", with respect to a cell, refers to a cell that is cultured in vitro. If an animal is described as containing isolated cells, then those isolated cells were cultured in vitro and then implanted into the animal.

The term "progeny" or "off-spring" refers to any and all future generations derived and descending from a particular animal or cell. Thus, the progeny an animal of any successive generation are included herein such that the progeny, the F1, F2, F3, generations and so on are included in this definition.

The phrase "transgenic animal" refers to an animal comprising cells containing foreign nucleic acid (i.e., recombinant nucleic acid that is not native to the animal). The foreign nucleic acid may be present in all cells of the animal or in some but not all cells of the animal. The foreign nucleic acid molecule is called a "transgene" and may contain one or many genes, cDNA, etc. By inserting a transgene into a fertilized oocyte or cells from the early embryo, the resulting transgenic animal may be fully transgenic and able to transmit the foreign nucleic acid stably in its germline. Alternatively, a foreign nucleic acid may be introduced by transferring, e.g., implanting, a recombinant cell or tissue containing the same into an animal to produce a partially transgenic animal. Alternatively, a transgenic animal may be produced by transfer of a nucleus from a genetically modified somatic cell or by transfer of a genetically modified pluripotential cell such as an embryonic stem cell or a primordial germ cell. A chimeric animal may have cells donated by another animal in the germline, in which case the progeny of the animal may be heterozygous for chromosomes in the donated cells. If the donated cells contain an exogenous nucleic acid (i.e., nucleic acid that is not endogenous to the cells), the progeny of the chimeric animal may be "transgenic", where a "transgenic" animal is an animal made up cells containing foreign nucleic acid (i.e., recombinant nucleic acid that is not native to the animal). The foreign nucleic acid molecule may be called a "transgene" herein.

The phrases "hybrid animal", "transgenic hybrid animal" and the like are used interchangeably herein to mean an animal obtained from the mating of a first animal having certain qualities with a second animal having certain qualities. For example, a hybrid animal of the present disclosure can refer to the transgenic progeny obtained from the mating of a transgenic first animal that produces a common light-chain with a second transgenic animal that produces a synthetic heavy-chain. A hybrid animal can be immunized and used as a source for the production of antigen-specific antibodies.

The terms "antibody" and "immunoglobulin" are used interchangeably herein. These terms are well understood by those in the field, and refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma (IgG1, IgG2, IgG3, IgG4), delta, epsilon and mu heavy chains or equivalents in other species. Full-length immunoglobulin "light chains" (of about 25 kDa or about 214 amino acids) comprise a variable region of about 110 amino acids at the NH2-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')2, and or other antibody fragments that retain specific binding to antigen, and monoclonal antibodies.

Antibodies may exist in a variety of other forms including, for example, Fv, Fab, and (Fab')2, as well as bi-functional (i.e. bispecific) hybrid antibodies (e.g., Lanzavecchia and Scheidegger, Eur. J. Immunol. 1987, 17(1):105-111) and in single chains (e.g., Huston et al., Proc. Natl. Acad. Sci. U.S.A. 1988, 85(16):5879-5883 and Bird et al., Science. 1988, 242(4877):423-426, which are incorporated herein by reference). (See, generally, Hood et al., "Immunology", Benjamin, N.Y., 2nd ed. 1984, and Hunkapiller and Hood, Nature. 1986, 323(6083):15-16).

Chimeric antibodies are antibodies whose light and heavy chain genes have been constructed, typically by genetic engineering, from antibody variable and constant region genes belonging to different species. For example, the variable segments of the genes from a chicken or rabbit monoclonal antibody may be joined to human constant segments, such as gamma 1 and gamma 3. An example of a therapeutic chimeric antibody is a hybrid protein composed of the variable or antigen-binding domain from a chicken or rabbit antibody and the constant or effector domain from a human antibody (e.g., the anti-Tac chimeric antibody made by the cells of A.T.C.C. deposit Accession No. CRL 9688), although other mammalian species may be used.

As used herein, the term "humanized antibody" or "humanized immunoglobulin" refers to a non-human antibody containing one or more amino acids (in a framework region, a constant region or a CDR, for example) that have been substituted with a correspondingly positioned amino acid from a human antibody. In general, humanized antibodies are expected to produce a reduced immune response in a human host, as compared to a non-humanized version of the same antibody.

It is understood that the humanized antibodies designed and produced by the present method may have additional conservative amino acid substitutions which have substantially no effect on antigen binding or other antibody functions. By conservative substitutions is intended combinations such as those from the following groups: gly, ala; val, ile, leu; asp, glu; asn, gln; ser, thr; lys, arg; and phe, tyr. Amino acids that are not present in the same group are "substantially different" amino acids.

The term "pseudogene" is used to describe an untranscribed nucleic acid region that contains an open reading frame that may or may not contain a start and/or a stop codon. An amino acid sequence may be "encoded" by a pseudogene in the sense that the nucleotide sequence of the open reading frame can be translated in silico to produce an amino acid sequence. In the context of the heavy and light chain immunoglobulin loci, pseudogenes do not contain promoter regions, recombination signal sequences or leader sequences.

The terms "upstream" and "downstream" are used with reference to the direction of transcription.

The term "specific binding" refers to the ability of an antibody to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

In certain embodiments, the affinity between an antibody and analyte when they are specifically bound in an antibody/analyte complex is characterized by a KD (dissociation constant) of less than 10-6 M, less than 10-7 M, less than 10-8 M, less than 10-9 M, less than 10-9 M, less than 10-11 M, or less than about 10-12 M or less.

A "variable region" of a heavy or light antibody chain is an N-terminal mature domain of the chain that contains CDR1, CDR2 and CD3, and framework regions. The heavy and light chain of an antibody both contains a variable domain. All domains, CDRs and residue numbers are assigned on the basis of sequence alignments and structural knowledge. Identification and numbering of framework and CDR residues is as described in by Chothia et al. and others (Chotia et al., J. Mol. Biol. 1998, 278(2):457-479).

VH is the variable domain of an antibody heavy chain. VL is the variable domain of an antibody light chain.

The terms "gene" and "locus" are used interchangeably herein. Neither term implies that a gene is actively transcribed or intact. Both terms encompass genes that have been inactivated.

As used herein, a "chimeric" chicken is a chicken containing a significant number of genetically distinct cells from at least two sources. A chimeric animal may be made by implanting cells from one animal into an embryo of another animal, or by implanting cultured cells (that, e.g., have a modified genome) into an embryo. The implanted cells may be harvested from a culture prior to incorporation into the host embryo. The embryo develops into an animal, and the resultant animal may contain cells from the host as well as the implanted cells. If the donated cells contain an exogenous nucleic acid (i.e., nucleic acid that is not endogenous to the cells), the progeny of the chimeric animal may be "transgenic", where a "transgenic" animal is an animal made up cells containing foreign nucleic acid (i.e., recombinant nucleic acid that is not native to the animal). The foreign nucleic acid molecule may be called a "transgene" herein.

The term "inactivated" is intended to indicate a gene that is not expressed in the sense that the protein encoded by the gene is not expressed. Genes can be inactivated by removing a portion of a coding sequence and/or regulator sequence of a gene. A gene that is disrupted, e.g., "knockout", is a type of inactivated gene. A locus that once contained an expressed endogenous sequence that has since been replaced by a human immunoglobulin sequence that is also expressed contains an inactivated endogenous gene. As such, a locus that contains an expressed human immunoglobulin sequence can have an inactivated endogenous immunoglobulin gene if the endogenous immunoglobulin gene was replaced by the human immunoglobulin sequence. In many case this may be done by knocking out the endogenous sequence (e.g., by deletion of at least part of the sequence) and then inserting the human immunoglobulin sequence at a position that was once occupied by the endogenous sequence.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide. If a cell receives a recombinant nucleic acid, the nucleic acid is "exogenous" to the cell.

The term "Cre" refers to a recombinase that effects site-specific recombination of DNA at lox sites (see definition below), as disclosed by Abremski et al., Cell. 1983, 32(4):1301-1311.

As used herein, the terms "recombinase" and "recombination sites" refer to a site-specific recombinase and its recognition site (e.g., Cre/lox, Flp-FRT, etc.,), where the recombinase is capable of excising sequence between two of its recognition sites.

The phrase "recombinase transgene" refers to a transgene that comprises a recombinase, e.g., Cre, coding sequence.

The phrase "recombinase-inducible" or "recombinase-inducible transgene" as used herein refers to a transgene that is non-functional until recombinase is expressed within the same cell. In some cases, expression of recombinase results in the excision of a sequence (e.g., intervening sequence) that normal prevents downstream sequences/genes from being expressed.

The phrase "Lox site" and "LoxP site" as used interchangeably herein refers to a nucleotide sequence at which Cre can catalyze a site-specific recombination. As is known the LoxP site is composed of two 13 base pair inverted repeats separated by an 8 base pair spacer region. Other suitable lox sites include LoxB, LoxL and LoxR sites which are nucleotide sequences isolated from *E. coli*. These sequences are disclosed and described by Hoess et al., Proc. Natl. Acad. Sci. U.S.A. 1982, 79(11):3398-3402. In some embodiments, the a lox site may be a LoxP, LoxC2, lox2272, lox5171, or lox511 site.

As used herein, the term "self-inactivating" (e.g., in the context of a self-inactivating recombinase transgene) refers to a gene that upon expression, has the ability to inactivate itself. For example, self-inactivating recombinase transgene of the present disclosure may be flanked by recombination, e.g., Lox, sites which, upon expression of recombinase, results in its own excision and self-inactivation.

The term "intervening sequence" as used herein refers to refers to a genetic sequence that, when inserted between two operably linked genetic elements, prevents those elements from being operably linked, wherein the intervening sequence is not naturally found between the two genetic elements. For example, an intervening sequence may be a sequence of nucleotides that is inserted between a promoter (e.g., a non-immunoglobulin light-chain promoter) and protein coding sequence (e.g., a coding sequence for a common light-chain) that prevents the protein coding sequence from being transcribed from the promoter. An intervening sequence may be flanked by recombination sites. In the presence of a suitable recombinase, the intervening sequence separating a promoter and a coding sequence may be excised, thereby placing the promoter and coding sequence in operably linkage and allowing the coding sequence to be transcribed.

The term "genetically linked" refers to two genetic elements that exist on the same chromosome such that there is a tendency for the genetic elements to be inherited together during meiosis (i.e., the elements have a recombination frequency of less than 50%, less than 40%, less than 30%, less than 20%, less than 10% or less than 5%). Two genetic elements that are linked closely to each other are less likely to be separated onto different chromatids during chromosomal crossover events (or "recombination"). The chance that two genetically linked elements become separated during recombination depends on the amount of sequence between the two elements, and can be calculated into a percentage of likelihood, termed "recombination frequency".

As used herein, the term "common light-chain" or "common immunoglobulin light-chain" refers to a light chain variable region that can pair with multiple heavy chain variable regions to produce antibodies that bind to different antigens. The common light chain is a passive partner for antigen binding, and antigen binding is determined by the heavy chains. For example, bi-specific antibodies have two binding specificities and, in some cases, both arms of a bi-specific antibody have the same light-chain (i.e., a "common" light chain) and different heavy chains (which largely determine the binding specificity of the arm).

A common light-chain of the present disclosure comprises a "pre-rearranged light-chain variable region" (or "pre-rearranged variable region"), wherein the light-chain variable region has a defined sequence and has been selected for properties that allows it to pair well with multiple heavy chain variable regions to produce antibodies of different specificities. A "common light-chain transgene" of the present disclosure may be a transgene that at least comprises a common light-chain coding sequence (or pre-rearranged light-chain variable region) and a light-chain constant region in one long open reading frame. This transgene may be a cDNA. Further definitions may be elsewhere in this disclosure.

DESCRIPTION OF EXEMPLARY EMBODIMENTS

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a cell" includes a plurality of cells and reference to "a candidate agent" includes reference to one or more candidate agents and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As noted above, a transgenic animal is provided. In certain embodiments, the animal may be any non-human animal that has a relatively small number of light chain genes, or an animal that employs gene conversion for developing their primary antigen repertoire and, as such, the animal may be any of a variety of different animals. In one embodiment, the animal may be a bird, e.g., a member of the order Galliformes such as a chicken or turkey, or a member of the order Anseriformes such as a duck or goose, or a mammal, e.g., a lagamorph such as rabbit, or a farm animal such as a cow, sheep, pig or goat. In particular embodiments, the transgenic animal may be a rodent (e.g., a mouse or rat), or a non-rodent (e.g., non-mouse or non-rat), non-primate transgenic animal.

Some of this disclosure relates to a transgenic chicken containing one or more transgenes. Since the nucleotide sequences of the immunoglobulin loci of many animals are known, as are methods for modifying the genome of such animals, the general concepts described below may be readily adapted to any suitable animal, particularly animals that employ gene conversion for developing their primary antigen repertoire. The generation of antibody diversity by gene conversion between the variable region of a transcribed immunoglobulin heavy or light chain gene and operably linked (upstream) pseudo-genes that contain different variable regions is described in a variety of publications such as, for example, Butler (Rev. Sci. Tech. 1998 17: 43-70), Bucchini (Nature 1987 326: 409-11), Knight (Adv. Immunol. 1994 56: 179-218), Langman (Res. Immunol. 1993 144: 422-46), Masteller (Int. Rev. Immunol. 1997 15: 185-206), Reynaud (Cell 1989 59: 171-83) and Ratcliffe (Dev. Comp. Immunol. 2006 30: 101-118).

In some embodiments, the genome of the transgenic animal is modified to contain a recombinase transgene, i.e., a recombinase (e.g., Cre) coding sequence, where the recombinase-coding sequence is operably linked to an endogenous immunoglobulin light chain promoter of the animal, where the term "endogenous immunoglobulin light chain promoter" is intended to be the immunoglobulin light chain promoter that is present at the immunoglobulin light chain locus in an unmodified animal. In other words, the recombinase transgene is placed downstream of the endogenous immunoglobulin light chain promoter in a way that the promoter drives expression of the recombinase in B cells and other cells that produce antibodies. This modification inactivates expression of the endogenous light chain coding sequences. The genome of the animal also contains a recombinase-inducible common light-chain transgene comprising a non-immunoglobulin light-chain promoter (e.g., a constitutive promoter, or another promoter that would be expected to be active in B cells), a coding sequence for a common light-chain (e.g., a cDNA encoding a common light chain), and an intervening sequence that prevents the common light-chain from being expressed, unless the intervening sequence is excised by the recombinase. As would be apparent, the intervening sequence can be flanked by recombination sites, e.g., lox sites and, as such, expression of recombinase in B cells excises the intervening sequence, thereby allowing expression of the common light chain by the non-immunoglonulin light-chain promoter.

In some embodiments, the recombinase transgene and the recombinase-inducible common light-chain transgene may be genetically linked to one another, but not at the same locus. For example, the recombinase transgene (which is inherently present at an immunoglobulin light chain locus) and the recombinase inducible common light-chain transgene may be separated from another by a distance of at least 100 kb, at least 200 kb, at least 300 kb, at least 400 kb, at least 500 kb or at least 1 Mb, thereby preventing the common light-chain coding sequence from being subjected to hypermutation, rearrangements and gene conversion (which would happen if the common light chain coding sequence were immediately adjacent to the recombinase transgene), but nevertheless linked on the same chromosome such that recombination between the recombinase transgene and the common light-chain transgene occurs at a relatively low frequency, i.e., a frequency of up to 10%, up to 5%, up to 2.5% or up to 1%. The linkage between the recombinase transgene allows mating strategies to work much more efficiently.

The transgenic animal may be heterozygous or homozygous for the recombinase transgene and the recombinase inducible common light-chain transgene, particularly if those transgenes are genetically linked. If the transgenic animal is heterozygous for the transgenes, then the other allele of the light chain locus may be inactivated, meaning that the only light chain produced by the animal will be the common light chain. See, e.g., US2010082759.

The heavy chain locus of the animal may be wild type, or it may have been modified. In some embodiments, the transgenic animal may have a genome that further comprises a "synthetic" immunoglobulin heavy chain (IgH) locus ("SynV") comprising: a) a functional IgH gene comprising a nucleic acid encoding a heavy chain variable region comprising: i) a heavy chain CDR1, CDR2 and CDR3 regions; and ii) a heavy chain framework; and b) a plurality of pseudogenes that encode heavy chain variable regions each comprising: i) a light chain CDR1, CDR2 and CDR3 regions; and ii) a heavy chain framework region that is identical in amino acid sequence to the heavy chain framework of a) (ii); wherein the recombinant IgH locus comprises: in operable linkage: an intron region, a constant domain region-encoding region and a 3' untranslated region; wherein at least part of the intron region is endogenous to the genome of said transgenic animal; and said nucleic acid of a) and pseudogene of b), are exogenous to the genome of said transgenic animal, wherein each amino acid residue of the CDRs encoded by the pseudogenes of b) and each amino acid residue of the CDRs of the light chain variable region of a) are selected from the same group of 2 to 5 amino acid residues, wherein said plurality of pseudogenes are operably linked to said functional IgH gene and donate nucleotide sequences to the nucleic acid of a) by gene conversion in said transgenic animal; and wherein said transgenic animal expresses a recombinant immunoglobulin comprising a diversified form of said functional IgH variable region. The at least one of the 2 to 5 amino acids in said group can be a tyrosine or tryptophan residue, and at least one of the 2 to 5 amino acids in the group may be an alanine, glycine or serine residue. In these embodiments, the heavy chain framework may be a human framework, e.g., may have an amino acid sequence that is identical to a human germline framework. The animal may be homozygous or heterozygous for the modified heavy chain locus. Further details of this may be found in in U.S. Pat. No. 8,592,644, which is incorporated by reference herein.

In some embodiments, the common light-chain coding sequence encodes a common immunoglobulin light-chain comprising a pre-rearranged variable region or a cDNA.

In some embodiments, the intervening sequence of the recombinase-inducible common light-chain transgene may contain a selectable marker cassette, e.g., a hygromycin resistance cassette, so that cells containing that construct can be selected. In these embodiments, the selectable marker cassette may contain a polyadenylation site that prevents downstream transcription.

The above-described transgenic animal may be made by modifying the genome of an animal recombinantly. Methods for producing transgenic animals, e.g., mice and chickens, etc. are known, and, in particular, methods for modifying the genomes of animal that use gene conversion are also known (see, e.g., Sayegh, Vet. Immunol. Immunopathol. 1999 72:31-7 and Kamihira, Adv. Biochem. Eng. Biotechnol. 2004 91: 171-89 for birds, and Bosze, Transgenic Res. 2003 12:541-53 and Fan, Pathol. Int. 1999 49: 583-94 for rabbits and Salamone J. Biotechnol. 2006 124: 469-72 for cow), as is the structure and/or sequence of the germline immunoglobulin heavy and light chain loci of many of those species (e.g., Butler Rev Sci Tech 1998 17:43-70 and Ratcliffe Dev Comp Immunol 2006 30: 101-118), the above-described animal may be made by routine methods given this disclosure. Methods for making transgenic chickens are known. See, e.g., U.S. Pat. Nos. 8,592,644, 8,889,662, Collarini et al (Poult Sci. 2015 94: 799-803), van de Lavoir (Nature. 2006 441: 766-9) and Schusser et al (Proc Natl Acad Sci USA. 2013 110: 20170-5.

Also provided is a method for producing antibodies that contains a common light-chain. In some embodiments this method may comprise: immunizing a transgenic animal as described above with antigen, and, if the antibodies are polyclonal, the method may comprise isolating the antibodies from a bleed from the animal. If the animal is homozygous for the common light chain sequence, then all of the antibodies in the polyclonal antisera should have the same light chain. If monoclonal antibodies are desired, then the method may comprise b) making hybridomas using cells of the immunized transgenic animal; c) screening the hybridomas to identify an antigen-specific hybridoma; and d) isolating an antigen-specific antibody from the antigen-specific hybridoma.

In certain embodiments, the animal may be immunized with: GD2, EGF-R, CEA, CD52, CD20, Lym-1, CD6, complement activating receptor (CAR), EGP40, VEGF, tumor-associated glycoprotein TAG-72 AFP (alpha-fetoprotein), BLyS (TNF and APOL-related ligand), CA125 (carcinoma antigen 125), CEA (carcinoembrionic antigen), CD2 (T-cell surface antigen), CD3 (heteromultimer associated with the TCR), CD4, CD11a (integrin alpha-L), CD14 (monocyte differentiation antigen), CD20, CD22 (B-cell receptor), CD23 (low affinity IgE receptor), CD25 (IL-2 receptor alpha chain), CD30 (cytokine receptor), CD33 (myeloid cell surface antigen), CD40 (tumor necrosis factor receptor), CD44v6 (mediates adhesion of leukocytes), CD52 (CAMPATH-1), CD80 (costimulator for CD28 and CTLA-4), complement component C5, CTLA, EGFR, eotaxin (cytokine A11), HER2/neu, HER3, HLA-DR, HLA-DR10, HLA ClassII, IgE, GPiib/iiia (integrin), Integrin aVβ3, Integrins a4β1 and a4β7, Integrin β2, IFN-gamma, IL-1β, IL-4, IL-5, IL-6R (IL6 receptor), IL-12, IL-15, KDR (VEGFR-2), lewisy, mesothelin, MUC1, MUC18, NCAM (neural cell adhesion molecule), oncofetal fibronectin, PDGFI3R (Beta platelet-derived growth factor receptor), PMSA, renal carcinoma antigen G250, RSV, E-Selectin, TGFbeta1, TGFbeta2, TNFα, DR4, DR5, DR6, VAP-1 (vascular adhesion protein 1) or VEGF, or the like in order to produce a therapeutic antibody.

The antigens can be administered to a transgenic host animal in any convenient manner, with or without an adjuvant, and can be administered in accordance with a predetermined schedule.

After immunization, serum or milk from the immunized transgenic animals can be fractionated for the purification of pharmaceutical grade polyclonal antibodies specific for the antigen. In the case of transgenic birds, antibodies can also be made by fractionating egg yolks. A concentrated, purified immunoglobulin fraction may be obtained by chromatography (affinity, ionic exchange, gel filtration, etc.), selective precipitation with salts such as ammonium sulfate, organic solvents such as ethanol, or polymers such as polyethyleneglycol.

For making a monoclonal antibody, antibody-producing cells, e.g., spleen cells, may isolated from the immunized transgenic animal and used either in cell fusion with transformed cell lines for the production of hybridomas, or cDNAs encoding antibodies are cloned by standard molecular biology techniques and expressed in transfected cells. The procedures for making monoclonal antibodies are well established in the art. See, e.g., European Patent Application 0 583 980 A1, U.S. Pat. No. 4,977,081, WO 97/16537, and EP 0 491 057 B1, the disclosures of which are incorporated herein by reference. In vitro production of monoclonal antibodies from cloned cDNA molecules has been described by Andris-Widhopf et al., J Immunol Methods 242:159 (2000), and by Burton, Immunotechnology 1:87 (1995), the disclosures of which are incorporated herein by reference.

If the antibody does not already contain human framework regions, the method may further include humanizing the antibody, which method may include swapping the constant domain of the antibody with a human constant domain to make a chimeric antibody, as well as in certain cases humanizing the variable domains of the antibody by e.g., CDR grafting or resurfacing etc. Humanization can be done following the method of Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/:US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, including references cited therein.

As such, in addition to the transgenic animal, a method comprising immunizing the transgenic animal with an antigen and obtaining from the transgenic animal an antibody that specifically binds to the antigen is also provided. The method may include making hybridomas using cells of the transgenic animal; and screening the hybridomas to identify a hybridoma that produces an antibody that specifically binds to the antigen.

Once monoclonal antibodies that bind to different antigen have been isolated, then bi-specific antibodies can be made using any convenient method. For example, two heavy chain sequences can be expressed in a single host cell along with a single common light chain, in which case a portion of the antibodies secreted by those cells should be bi-specific. Alternatively, two heavy chains and the common light chain may be separately expressed and folded or joined together in vitro.

In the case of an animal that has a synthetic VH, all of the antibodies produced by the animal should have a common light chain and a heavy chain which, except for a relatively small number of amino acids that have resulted from non-gene conversion based amino acid changes to the variable domain in the functional gene during affinity maturation (i.e., which occur in less than 10%, less than 5, less than 3%, or less then 1% of the amino acids), the CDRs are composed the 2-5 amino acids encoded by locus described above. Likewise, the framework region is comprised of the predetermined sequence known to have desirable attributes such as monomeric form, ease of manufacturing, high solubility, and thermodynamic stability.

The heavy chains variable domain of the antibodies are made "naturally" by the immune system of the animal. Such antibodies may, in certain case, be post-translationally modified (e.g., glycosylated) by the host cell and may have a glycosylation pattern and composition characteristic of the species of transgenic animal.

In certain embodiments, an antibody produced by the transgenic animal is provided, where the antibody comprises: a constant domain linked to a variable domain, wherein the variable domain comprises: a) a common light chain variable domain and a) a heavy chain variable domain comprising: i. heavy chain CDR1, CDR2 and CDR3 regions that are composed of the 2 to 5 different amino acids; and ii. heavy chain framework regions.

EXAMPLES

The following examples are provided in order to demonstrate and further illustrate certain embodiments and aspects of the present invention and are not to be construed as limiting the scope thereof.

Some of the principles of the present disclosure are illustrated in the following example. As would be apparent, the principle applied to VK genes below can be applied to other light chain genes.

Example 1

Figure 2:
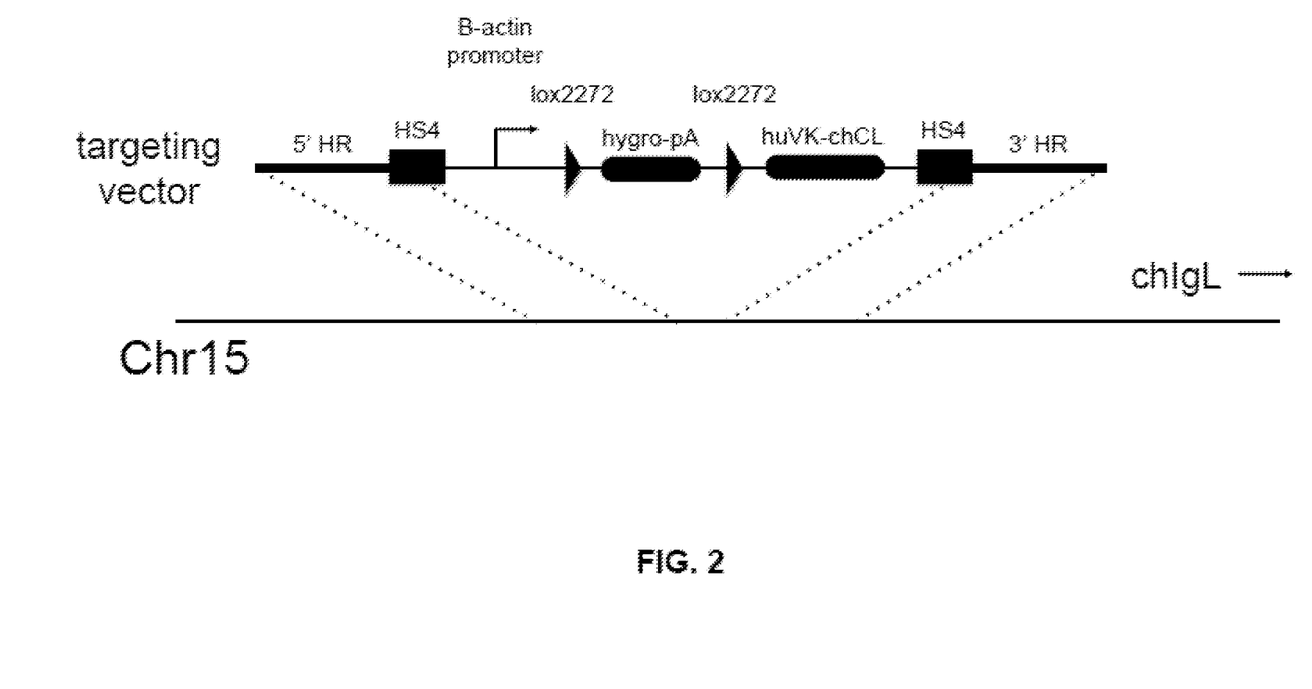
FIG. 2 depicts a schematic demonstrating the targeting of a conditional human VK to an intergenic region on chromosome 15.

Making a Transgenic Chicken with a Common Light Chain That Does Not Undergo Mutation Since the mechanisms of antibody diversification in B cells are mainly confined to genes in the immunoglobulin loci, one approach to making a transgenic chicken with a common light chain that does not undergo mutation was to insert the light chain in another locus in the genome, under transcriptional control of non-immunoglobin control elements (FIG. 1). B cell-specific expression was achieved using a conditional transgene that was activated upon Cre-mediated recombination only in B cells. To achieve Cre recombination only in B cells, Cre expression was made B cell-specific by inserting the Cre gene in the light chain locus (FIG. 2). Upon induction of Cre expression by the light chain regulatory elements in early B cell development, Cre recombinase activity looped out a stop sequence that blocks expression of the common light chain.

Figure 3:
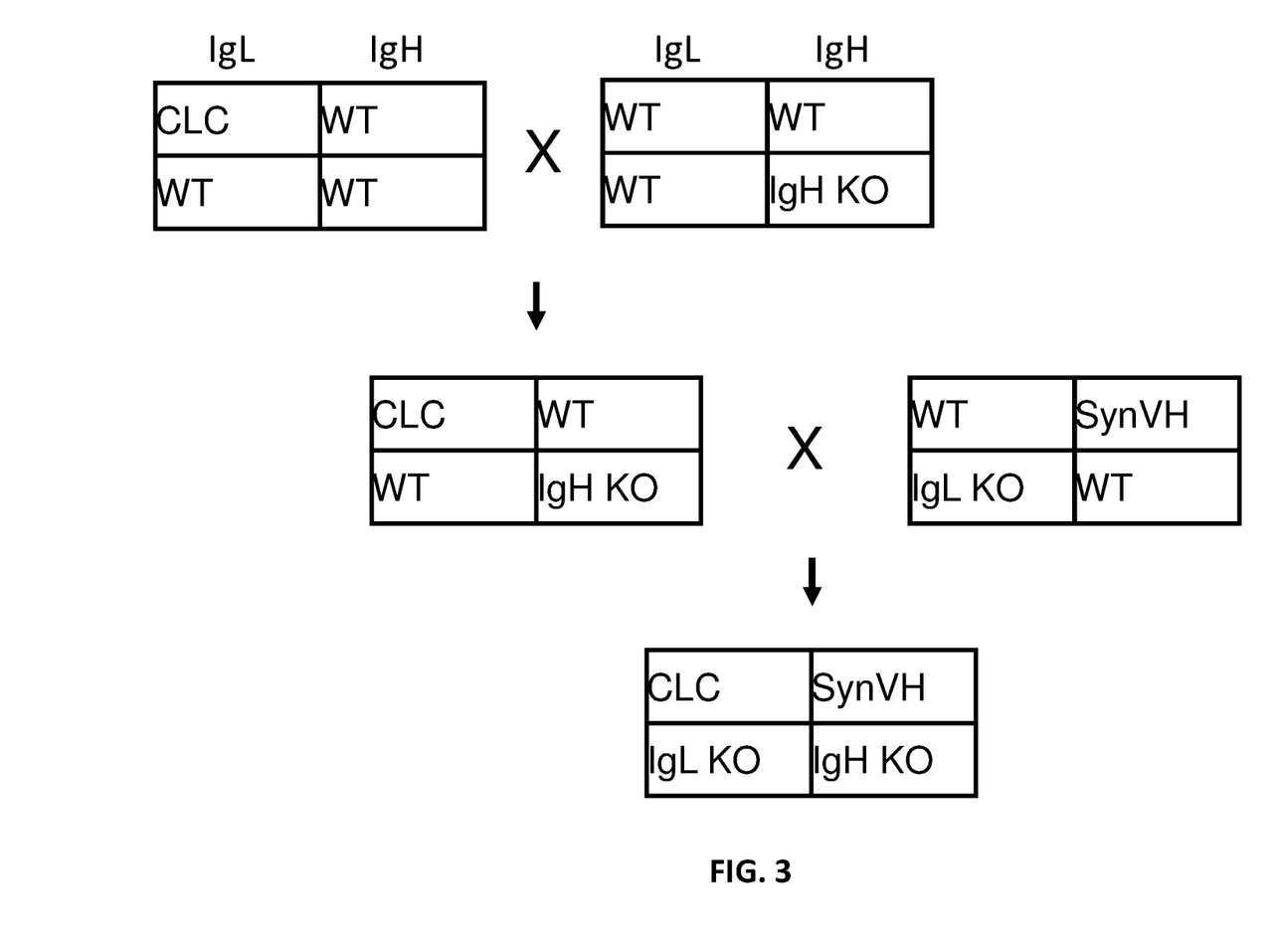
FIG. 3 depicts some breeding strategies of the present disclosure.
Figure 4:
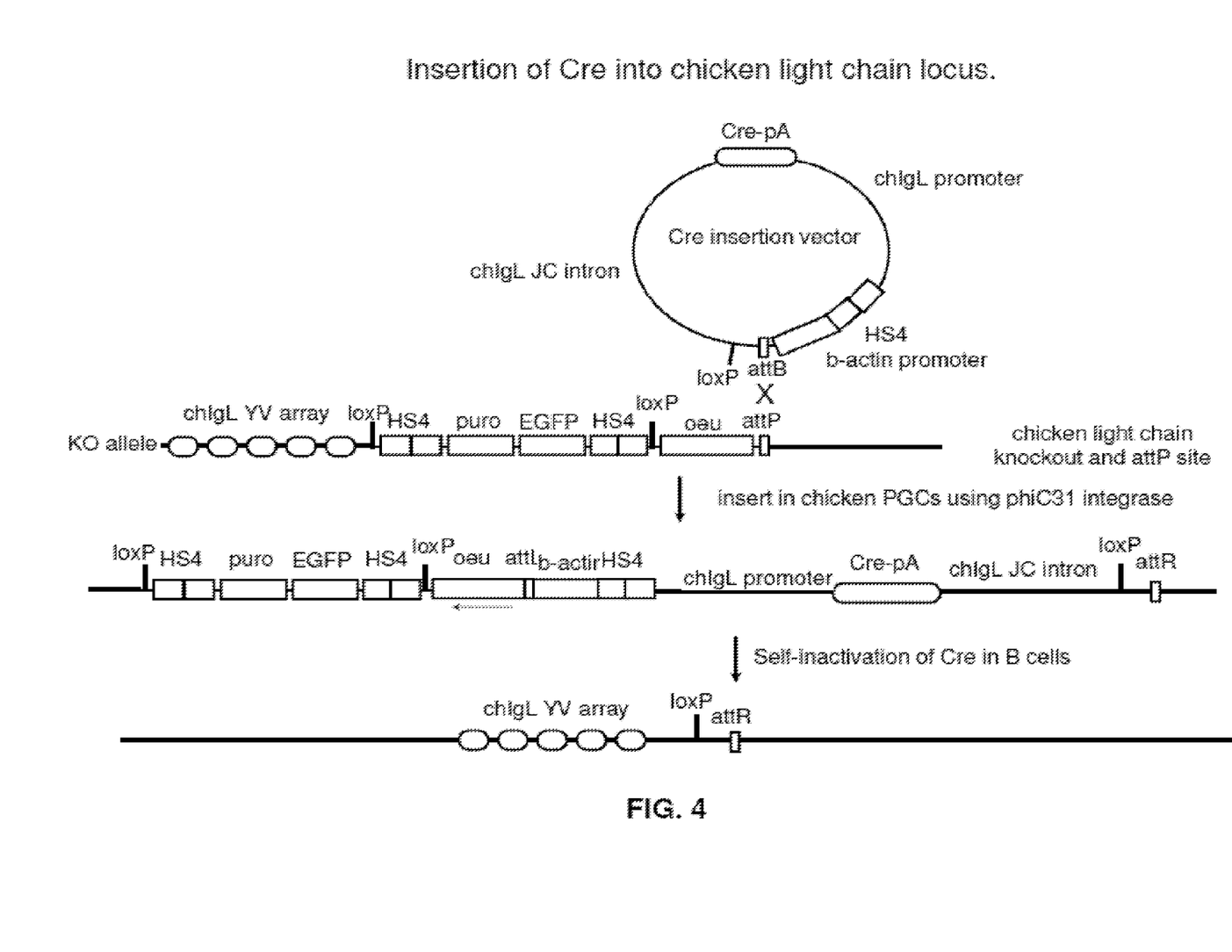
FIG. 4 depicts a schematic demonstrating the strategy for the insertion of a self-inactivating Cre into the chicken light chain locus.

An alternative approach could be to insert the pre-rearranged V region in the light chain locus, and remove all pseudogenes upstream, eliminating the possibility of gene conversion (FIGS. 3 and 4).

Example 2

Screening a Light Chain Library for a Pre-Rearranged Human VK Common Light Chain That Pairs and Expresses with Crystal's Human Heavy Chain A human pre-rearranged light chain variable region may be identified that pairs well with the human heavy chain variable region that has been selected. A library of human VK3 family sequences is co-transfected into 293 cells with an expression construct bearing Crystal's human VH3-23 gene. Culture supernatants are screened by ELISA for levels of IgG produced. A human VK sequence that most closely resembles the germline sequence is preferred. This human VK gene is referred to as the common light chain. The common light chain gene contains the human VK region and chicken light chain constant region in one long open reading frame. No introns are necessary.

Example 3

Insertion of Pre-Rearranged Human VK Gene (Common Light Chain) Into Chicken Chromosome 15

The human VK common light chain is driven by the chicken B-actin promoter or the CAG promoter to ensure high levels of expression in B cells (FIG. 3). Since it is desirable to have high-level expression of the common light chain in B cells only, the transgene is activated by Cre recombination. A hygromycin-resistance cassette flanked by lox2272 sites is placed between the promoter region and the common light chain gene such that the promoter drives expression of the hygromycin-resistance gene prior to Cre recombination. Upon Cre expression, the hygro gene is excised, leaving behind a single lox2272 site, allowing the promoter to drive expression of the common light chain. The construct also contains HS4 sites from the chicken B-globin locus which act as chromatin insulators.

Figure 7:
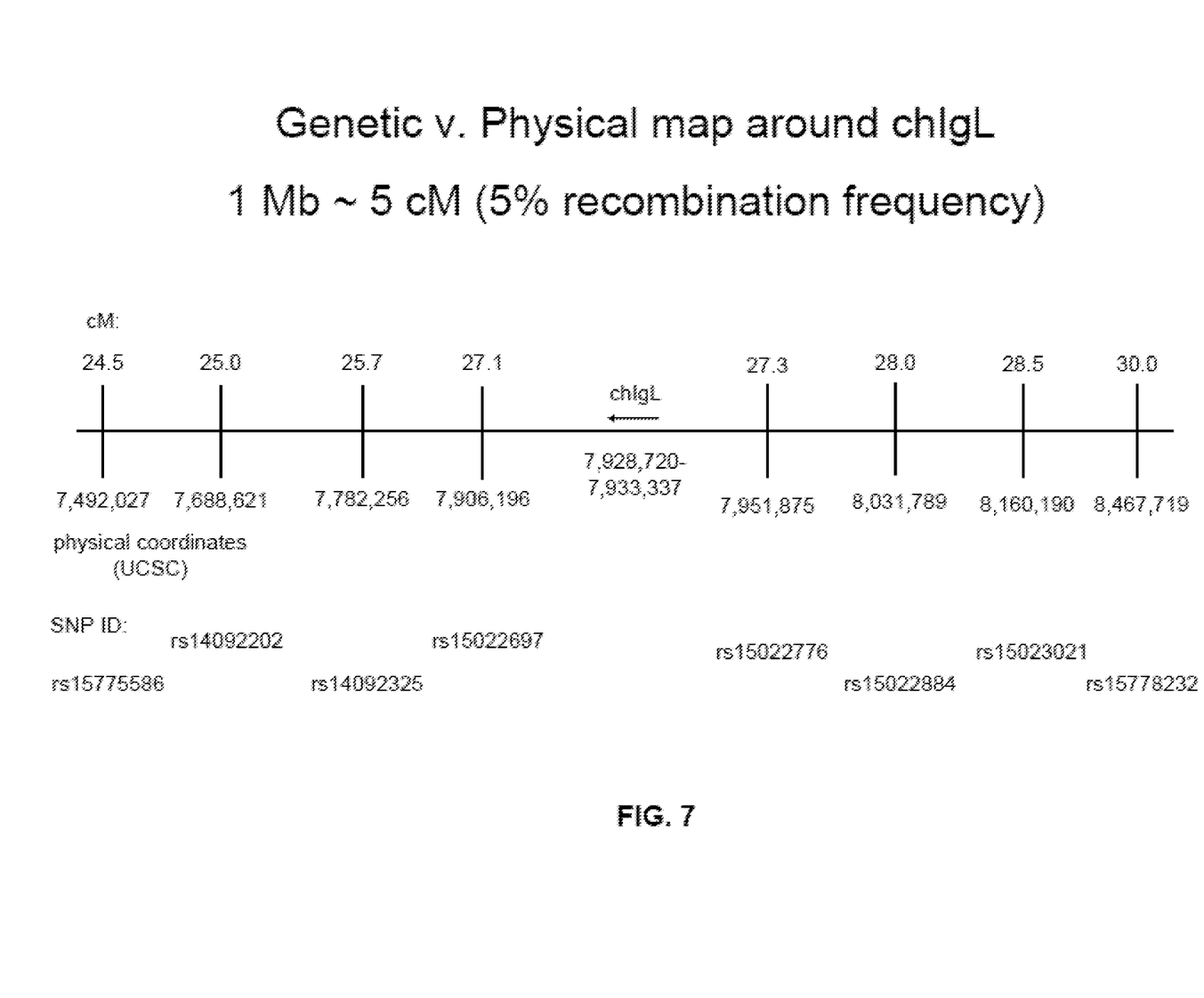
FIG. 7 depicts the genetic and physical map surrounding chicken light chain locus. 1 Mb is approximately 5 cM (5% recombination frequency).

The common light chain transgene is inserted into chromosome 15 by homologous recombination using isogenic DNA targeting arms. The location of the insertion is chosen to be close enough to the endogenous light chain locus so that the breeding strategies downstream are simplified, since both the IgL-Cre and common light chain transgenes need to be present. On chicken chromosome 15 surrounding the light chain locus, 500 kb equates roughly to 2.5 cM or a 2.5% recombination frequency. Placement of the common light chain gene within 500 kb of the chicken light chain locus thus ensures that the common light chain transgene and the Cre transgene (see below) remain linked about 98% of the time (FIG. 7). An intergenic region less than or about 500 kb from the endogenous light chain locus is chosen for insertion of the common light chain. It is desired not to be too close to the endogenous light chain locus so as to avoid potential mutational mechanisms that might increase the mutation rate of the common light chain transgene. The IgL-Cre/common light chain chromosome or haplotype is inherited essentially as a unit, greatly simplifying downstream breeding strategies needed to bring together the heavy chain transgenes with the common light chain in order to produce fully human antibodies.

The targeting construct to insert the common light chain into chromosome 15 contains 5' and 3' homology regions isogenic to the PGC cells used for targeting. The homology regions are amplified from genomic DNA from a bird that is homozygous for the light chain locus present in the cells, to ensure that the sequences are isogenic to that chromosome. These cells have been used for previous light chain knockout and knock-in transgenes and birds have been produced by germline transmission of the cells. Intercrossing heterozygous birds has produced homozygous birds carrying the light chain locus and closely linked sequences (such as the region chosen for targeting) on both chromosomes. Cloning the homology regions from homozygous DNA ensures that the sequences are from the same chromosome as the light chain that we have previously targeted. In chicken PGCs, it is required that the homology regions match the genome exactly, and even a few single nucleotide changes in the homology regions inhibits or severely reduces the frequency of targeting. Since chickens are not inbred, the PGC cells that are used for targeting contain two different sets of chromosomes that carry extensive single nucleotide polymorphisms relative to each other, and it is assured that homology regions that match one allele will contain polymorphisms relative to the other allele. Because of the requirement for exact sequence homology, targeting vectors designed for a specific allele only target that allele. Homology regions of at least 4 kb total length are sufficient for targeting. Alternatively, shorter homology regions of 1-2 kb total in combination with CRISPR to make a double strand break adjacent to the targeted region can also be used.

A ubiquitous, strong promoter such as chicken B-actin or CAG (B-actin plus CMV intermediate-early enhancer) is used. For selection of the targeting event in PGCs and to act as a Stop sequence to block expression of the common light chain in non-B lineage cells, the hygromycin resistance cassette is placed between the promoter and common light chain. The hygromycin cassette contains a polyadenylation site so that the common light chain gene is not transcribed. In the event of a long transcript being made containing both the hygromycin gene and the common light chain, the long open reading frame and stop codon of the hygro gene would prevent translation of the common light chain. Alternative loxP sites such as lox511, lox2272, or lox5171 flank the hygromycin cassette. It is important to use mis-matched loxP sites around the self-inactivating Cre and the common light chain so that there is no recombination between the two transgenes.

Chickens bearing the IgL-Cre/common light chain chromosome are bred to chickens carrying other transgenes, such as the IgL knockout and various heavy chain transgenes (FIG. 4). Breeding to IgL knockout chickens produces birds that have a homozygous functional knockout of the endogenous chicken light chain (one allele has the simple knockout, the other allele has the IgL-Cre transgene). The common light chain is the only light chain expressed in these chickens. Birds containing the IgL-Cre/common light chain chromosome are crossed to the heavy chain knockout to produce birds containing the common light chain and human heavy chain knockout. These birds are bred to birds containing the light chain knockout and a human heavy chain knock-in to produce birds with the genotype: common light chain/IgL knockout; human heavy chain knock-in/IgH knockout (FIG. 4).

Alternatively, the human VK transgene is inserted at random in the genome using phiC31 integrase.

Example 4

Cre Recombinase Knock-In Into the Chicken IGL Locus to Make IGL-Cre

Figure 5:
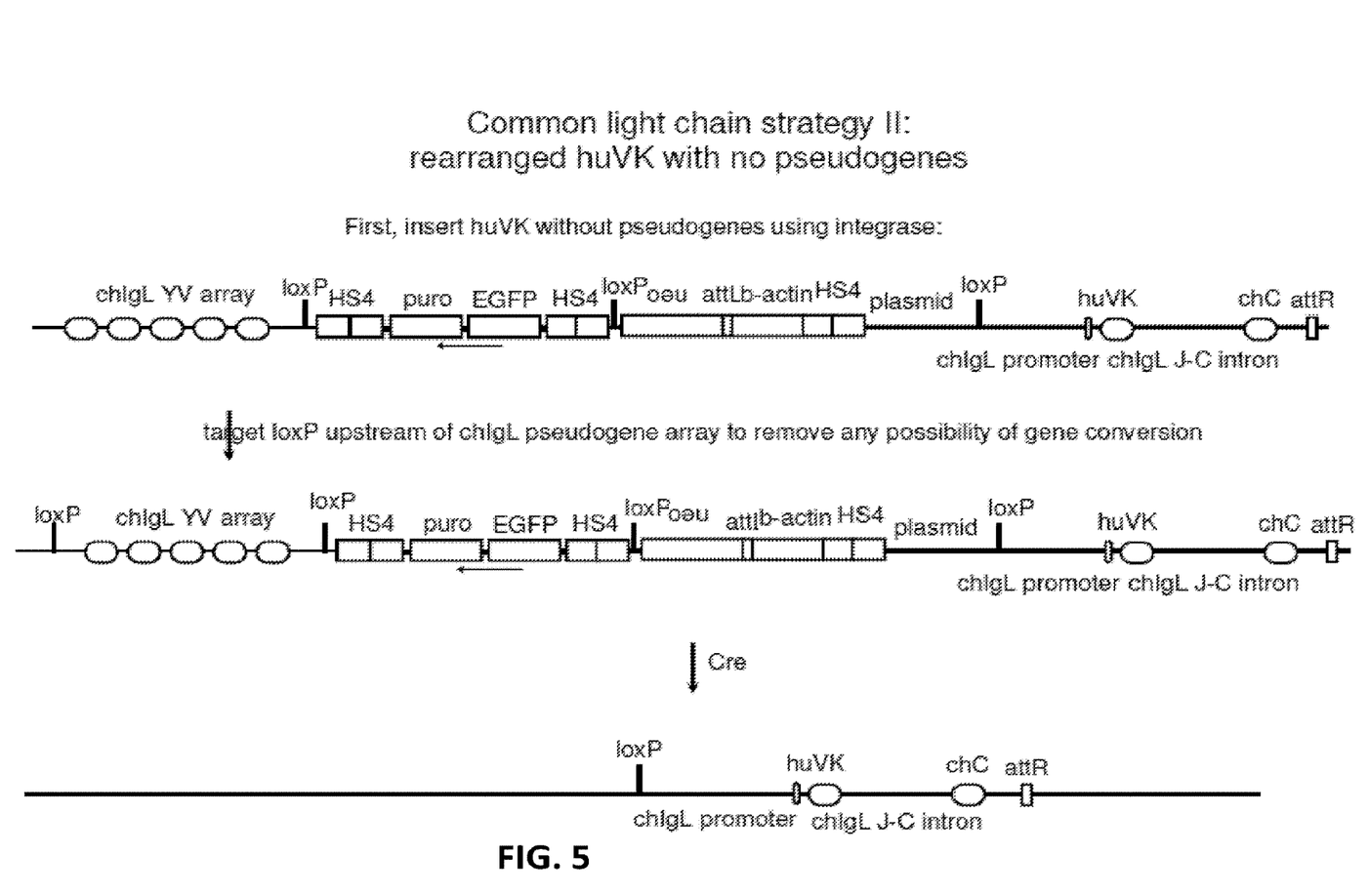
FIG. 5 depicts a schematic demonstrating insertion of a re-arranged human VK and the removal of pseudogenes.
Figure 6:
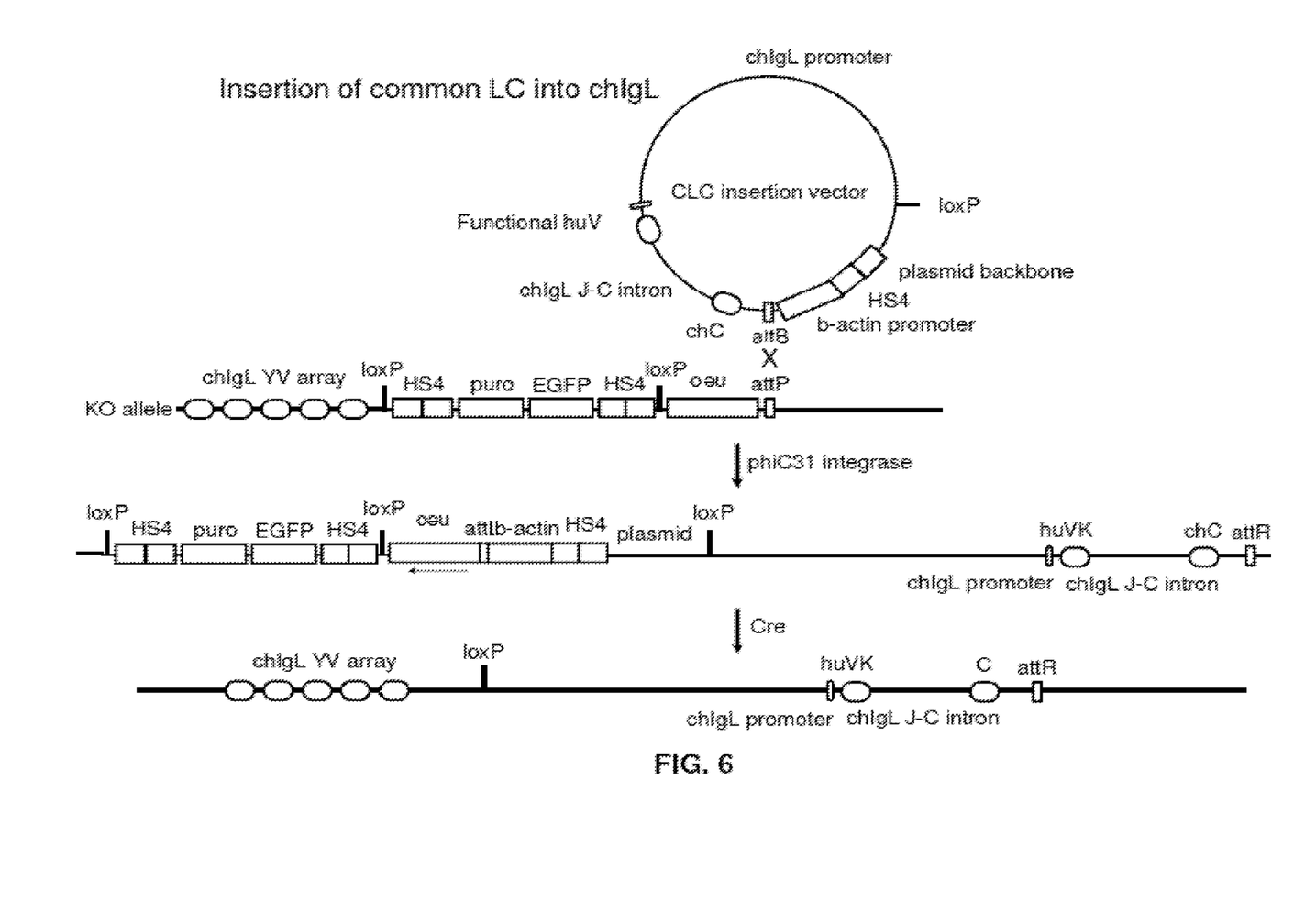
FIG. 6 depicts a schematic of a strategy for the insertion of the common light-chain transgene and Cre-inducible expression of the common light chain.

To make Cre expression B-cell specific, the Cre gene is inserted into the chicken light chain locus where its expression is driven by the light chain promoter and enhancer elements (FIG. 5). In chickens, the light chain and heavy chain genes both rearrange and express at the same time in early B cell development, and there is no surrogate light chain. Thus expression from the light chain locus is consistent with the stages of B cell development in which B cell receptor expression is critical. To insert Cre into the light chain locus, first an attP site is targeted to the locus which serves as a docking site for insertion using phiC31 integrase. Crystal has made a light chain knockout in which an attP site and promoterless neo gene were inserted by homologous recombination into the light chain locus, replacing the V, J and C coding regions, and the introns. The Cre insertion construct contains the Cre gene linked to the chicken light chain promoter for B-cell specific expression, and an attB site linked to a B-actin promoter. Upon insertion of the construct into the attP site at the light chain locus, the B-actin promoter drives expression of the neo gene, facilitating selection of the correct integration with G418. The Cre gene is then under the transcriptional control of the endogenous light chain promoter and enhancer elements in the locus, providing for B-cell specific expression. The construct contains, in order: attB site, B-actin promoter, two copies of the B-globin HS4 chromatin insulator, chicken IgL promoter, gene encoding Cre recombinase, rabbit globin polyA signal, chicken IgL JC intron, loxP site. Insertion of the Cre construct leads to a rebuilt light chain locus in which the V and J regions are replaced with Cre and the JC intron is replaced, but the constant region is absent.

The Cre gene can also be self-inactivating, so that Cre is only transiently expressed in the B-cell lineage. LoxP sites are placed on either side of the Cre gene so that the Cre recombinase produced upon induction of expression in the B cell lineage excises the Cre gene. In this case, variant loxP sites (such as lox511, lox2272, or lox5171) are used to flox the hygromycin cassette in the human VK transgene so that they don't recombine with the classical loxP sites flanking Cre at the light chain locus.

What is claimed is:
1. A transgenic chicken comprising B cells having a genome in which
   i. the endogenous functional light chain variable region coding sequence in the endogenous immunoglobulin light chain gene is replaced by an exogenous coding sequence encoding a pre-rearranged human immunoglobulin light chain variable region, and
   ii. the upstream pseudogenes of the endogenous light chain gene do not diversify the pre-rearranged human light chain variable region,
   wherein the chicken produces a diversified population of antibodies that have the same light chain variable region except for amino acid substitutions that have resulted from non-gene conversion events.

2. The transgenic chicken of claim 1, wherein the exogenous coding sequence is operably linked to an endogenous immunoglobulin light-chain promoter.

3. The transgenic chicken of claim 1, wherein the transgenic chicken is homozygous for the pre-rearranged human light chain variable region.

4. A method of producing a hybrid chicken comprising:
   mating a transgenic chicken that produces a common light-chain with a second transgenic chicken comprising a genome comprising a synthetic heavy-chain knock-in; and
   collecting the progeny of the mating.

5. The method of claim 4, wherein the synthetic heavy-chain knock-in is a human heavy-chain knock-in.

6. A method for producing an antibody with a common light-chain, wherein said antibody is specific for an antigen, said method comprising:
   a) immunizing a transgenic chicken of claim 1 with said antigen;
   b) making hybridomas using cells of said immunized transgenic chicken;
   c) screening said hybridomas to identify an antigen-specific hybridoma; and
   d) isolating an antigen-specific antibody from said antigen-specific hybridoma.

7. The method of claim 6, wherein the synthetic heavy-chain is a synthetic human heavy-chain.

* * * * *